(12) United States Patent
Watson

(10) Patent No.: US 7,501,112 B2
(45) Date of Patent: *Mar. 10, 2009

(54) GUARD BED CONTAINING LEAD COMPOUNDS UPSTREAM OF A BED OF COPPER-CONTAINING CATALYST TO PREVENT ITS CONTAMINATION BY CHLORINE AND SULPHUR CONTAMINANTS

(75) Inventor: Michael J. Watson, Stockton-on-Tees (GB)

(73) Assignee: Johnson Matthey PLC, London (GB)

( * ) Notice: Subject to any disclaimer, the term of this patent is extended or adjusted under 35 U.S.C. 154(b) by 369 days.

This patent is subject to a terminal disclaimer.

(21) Appl. No.: 11/386,763

(22) Filed: Mar. 23, 2006

(65) Prior Publication Data

US 2006/0166817 A1 Jul. 27, 2006

Related U.S. Application Data

(60) Division of application No. 10/087,944, filed on Mar. 5, 2002, now Pat. No. 7,098,167, which is a continuation of application No. PCT/GB00/03133, filed on Aug. 11, 2000.

(30) Foreign Application Priority Data

Sep. 6, 1999 (GB) .................................. 9920871.2

(51) Int. Cl.
*C01B 3/02* (2006.01)
*C01B 3/12* (2006.01)
*C01B 3/16* (2006.01)
*C01B 31/20* (2006.01)

(52) U.S. Cl. .............. 423/648.1; 423/415.1; 423/437.1; 423/437.2; 423/655; 423/656

(58) Field of Classification Search ............. 423/415.1, 423/437.1, 437.2, 648.1, 655, 656
See application file for complete search history.

(56) References Cited

U.S. PATENT DOCUMENTS

| 3,812,652 | A | 5/1974 | Carr et al. | |
|---|---|---|---|---|
| 4,026,698 | A | 5/1977 | Koump | |
| 4,683,218 | A | 7/1987 | Slaugh | |
| 4,849,576 | A | 7/1989 | Nowack et al. | |
| 4,849,577 | A | 7/1989 | Boitiaux et al. | |
| 5,120,511 | A | 6/1992 | Luft | |
| 7,087,550 | B2* | 8/2006 | Watson | ........................ 502/174 |
| 2004/0072682 | A1 | 4/2004 | Watson | |

FOREIGN PATENT DOCUMENTS

| EP | 0145288 | 6/1985 |
|---|---|---|
| GB | 1357335 | 6/1974 |

* cited by examiner

*Primary Examiner*—Elizabeth D Wood
(74) *Attorney, Agent, or Firm*—Jones Day

(57) ABSTRACT

A combination comprising a bed of a particulate copper-containing catalyst and, a guard bed of a particulate composition containing a) lead and/or at least one lead compound that reacts with hydrogen chloride and b) a support therefor. The lead compound is preferably lead nitrate. The combination is of particular utility for the low temperature shift reaction wherein carbon monoxide is reacted with steam to produce hydrogen and carbon dioxide.

7 Claims, No Drawings

GUARD BED CONTAINING LEAD COMPOUNDS UPSTREAM OF A BED OF COPPER-CONTAINING CATALYST TO PREVENT ITS CONTAMINATION BY CHLORINE AND SULPHUR CONTAMINANTS

CROSS REFERENCE TO RELATED APPLICATIONS

This application is a Divisional of U.S. Ser. No. 10/087,944, filed Mar. 5, 2002, which granted on Aug. 29, 2006 as U.S. Pat. No. 7,098,167, which further is a Continuation of International Application No. PCT/GB2000/003133, filed Aug. 11, 2000, which designates the United States and was published in English. These applications, in their entirety, are incorporated herein by reference.

This invention relates to catalysts and in particular to copper catalysts.

Copper catalysts are often employed for reactions involving hydrogen, for example simple hydrogenation reactions and for methanol synthesis (where carbon oxides are reacted with hydrogen), methanol decomposition (where methanol, often in admixture with steam, is decomposed to form hydrogen and carbon oxides) and the shift reaction (where carbon monoxide is reacted with steam to produce hydrogen and carbon dioxide) and the reverse shift reaction. Often, in order to obtain the optimum activity and stability of the catalyst, the catalyst is made with the copper in a highly dispersed form, for example by precipitation of a copper compound in the presence of, or together with, one or more support materials, especially zinc, magnesium, chromium and/or aluminium compounds. Following such precipitation, the composition is heated to convert the copper compounds, and, if necessary also support materials, to the corresponding oxides. Prior to use for the desired reaction, the copper oxide is reduced to metallic copper. Particularly suitable catalysts for the above reactions are copper/zinc oxide/alumina and copper/zinc oxide/chromia compositions. In some cases part of the zinc may be replaced by magnesium and/or part of the alumina or chromia may be replaced by ceria or a rare earth such as lanthana.

The copper catalysts are readily de-activated by the presence of chlorine compounds, such as hydrogen chloride, in the process gas undergoing the reaction. Traces of such chlorine compounds may arise from contaminants in the materials, for example hydrocarbon feedstock, steam, air, employed to make the process gas. Such chlorine compounds react with the active copper forming copper chloride. Since copper chloride is relatively low melting, at the temperatures at which the catalysts are commonly employed, e.g. 150-300° C., the copper is mobilised and tends to aggregate resulting in a loss of dispersion of the copper and consequent loss of activity of the catalyst. Also where zinc and/or magnesium oxide is a component of the catalyst, likewise the corresponding chlorides may be formed, and these likewise are liable to be mobilised resulting in loss of the stabilising effect of the zinc or magnesium oxides, again with the consequent loss of dispersion and activity of the copper.

In order to overcome this problem it has been proposed in GB 1 357 335 to provide a guard bed upstream of a copper shift catalyst, the guard bed comprising solid particles of, or containing, a material that is more basic than zinc oxide. Examples of guard beds proposed are oxides of alkali metals, alkaline earth metals, manganese, yttrium or lanthanum, supported on alumina particles. It is also known to use part of the copper-containing catalyst as a sacrificial guard bed.

However, where the process gas contains steam, as in the case of the aforesaid shift and methanol decomposition reactions, there is a risk that under certain conditions, e.g. plant upsets, water will condense on the guard bed and/or catalyst. In such circumstances chlorides formed by reaction of the basic material in the guard bed with the chlorine contaminants of the process gas may be washed out of the guard bed into the catalyst, again giving a loss of dispersion and activity of the catalyst.

We have found an alternative guard bed material that decreases such risk of de-activation of the catalyst.

Accordingly we provide a combination comprising a bed of a particulate copper-containing catalyst and, upstream of the catalyst bed, a guard bed of a particulate composition containing a) lead and/or at least one lead compound that reacts with hydrogen chloride and b) a support therefor.

The invention also provides a process wherein a process gas is subjected to a catalytic reaction using a bed of a copper-containing catalyst comprising passing the process gas through an guard bed as aforesaid prior to passage through the bed of the copper-containing catalyst.

In the present invention, lead and/or a lead compound that reacts with hydrogen chloride is employed in the guard bed. The lead compound may be lead oxide and/or a lead compound that decomposes upon heating to lead oxide, although, as described below, it is preferred to employ a lead compound that undergoes decomposition to lead oxide, or reduction by hydrogen-containing gas streams to elemental lead, only slowly at temperatures below 300° C., particularly below 350° C. and most preferably below 400° C. Preferred lead compounds include lead nitrate, lead carbonate, basic lead carbonate and lead "aluminate".

Thus we have found that a support impregnated with lead nitrate, dried and calcined at 300° C. for 2 hours gives superior performance to a similar material made using lead acetate. It is believed that the improved results arise since the lead nitrate does not undergo significant decomposition when heated at 300° C. for 2 hours and the heated material does not undergo significant reduction when treated with a hydrogen/carbon monoxide mixture at about 225° C. In contrast, a similar material made using lead acetate in place of lead nitrate and heated for 2 hours at 300° C. showed evidence of metallic lead after treatment with a hydrogen/carbon monoxide gas mixture at 225° C. Accordingly it is preferred that the lead compound is one that does not undergo significant decomposition when heated for 2 hours at 300° C. or reduction to elemental lead when treated with a hydrogen/carbon monoxide mixture at 225° C.

Also particularly effective is a product prepared by co-precipitating lead and aluminium compounds from an aqueous solution of soluble lead and aluminium salts. XRD analysis of such a product reveals that at least some of the lead may be present as a lead "aluminate" having a structure analogous to the magnesium aluminate $Mg_4Al_2(OH)_{14}.3H_2O$ and as a lead oxide/hydroxide $3PbO.2Pb(OH)_2$.

The support may be particles of an inert material such as alumina, chromia, zirconia, titania, or, less preferably, silica. The support preferably has a relatively high surface area, e.g. above 50 m²/g. In order to provide an adequate guard effect without the need for an excessive volume of guard bed particles, the guard bed particles preferably have a lead content of at least 2% by weight, more preferably at least 5% by weight, particularly at least 10% by weight, and most particularly at least 15% by weight. The guard bed particles may be made by impregnating preformed shaped particles, e.g. spheres or cylinders, of the support with a solution of a suitable lead salt, followed by heating to remove the water and/or treatment with a suitable reagent, including heating as necessary, to convert the lead salt to the desired lead compound. Examples of suitable reagents include urea, and ammonium or alkali metal, especially sodium, carbonates. Alternatively, the guard bed particles may be made by precipitating the lead compound in the presence of the support particles or by co-precipitating lead and support, or support precursor, compounds followed by heating as necessary and forming the precipitated compounds into shaped particles before or after such a heating step.

A preferred guard bed material is a particulate composition comprising lead nitrate and a support, especially an oxidic support such as alumina, therefor.

The guard bed particles preferably have maximum and minimum dimensions in the range 1.5 to 20 mm, particularly 3 to 6 mm.

The guard bed and the catalyst bed are used as fixed beds and may be in the same vessel or in different vessels, with the guard bed upstream of the catalyst bed. Preferably the process gas flows down through the catalyst bed: thus where the guard and catalyst beds are in the same vessel, the guard bed will be a layer of the guard bed particles on top of the catalyst bed particles. If desired there may be a layer of an inert material between the guard bed and the catalyst bed to facilitate replenishment of the guard bed without disturbing the catalyst bed.

The invention is of particular utility in relation to the shift reaction. In this process a process gas stream containing carbon monoxide and steam, and often other components such as hydrogen, carbon dioxide, methane, and/or nitrogen, is passed through a bed of the copper-containing catalyst, especially a copper/zinc oxide/alumina or copper/zinc oxide/chromia catalyst in which some of the zinc oxide may be replaced by magnesia and/or some of the alumina and/or chromia may be replaced by a rare earth, at a temperature in the range 150 to 300° C., especially at an inlet temperature in the range 150 to 250° C. The process gas preferably contains 1 to 4% by volume of carbon monoxide, and at least one mole of steam per mole of carbon monoxide. Preferably the process gas contains 20 to 50% by volume of steam. Typically the process is operated at a wet gas space velocity in the range 2000 to 5000 h$^{-1}$, and at a pressure in the range 10 to 50 bar abs.

In addition to absorbing chloride, it will be appreciated that the lead species will also absorb sulphur compounds and so the bed will also act as a sulphur guard bed.

The invention is illustrated by the following examples in which various guard beds were tested by charging 0.393 ml (0.50 g) of particles of a standard copper oxide/zinc oxide/alumina low temperature shift catalyst precursor containing about 50% by weight of copper oxide and having a particle size in the range 0.6-1.0 mm to a microreactor with a layer of particles of fused alumina (0.25 g) of particle size 0.6-1.0 mm on top of the shift catalyst precursor and 0.197 ml of the guard material particles of particle size 0.6-1.0 mm on top of the fused alumina particles to give a total catalyst bed of volume of 0.70 ml.

The copper oxide in the catalyst precursor was reduced to metallic copper by passing a stream of nitrogen containing 2% by volume of hydrogen down through the microreactor at a pressure of about 28 bar abs. at a flow rate of 15 litres/hour (at NTP) while the microreactor was heated from ambient temperature to 220° C. and held at this temperature for 95 minutes to give a total reduction time of 3.5 hours.

The catalyst activity for the water gas shift reaction was determined by passing 50 litres/hour (at NTP) of a gas mixture comprising 1 part by volume of steam to 2 parts by volume of a gas of volume composition H$_2$ 55%, CO$_2$ 15%, CO 5%, and N$_2$ 25% through the microreactor at a temperature of 220° C. and a pressure of about 28 bar abs.

To simulate chloride contamination, after the gas mixture had been passed through the catalyst bed for about 6 hours, HCl was added to the gas mixture to give an HCl concentration in the wet gas of 5.2 ppm by volume (test method 1) and 1 ppm by volume (test method 2). Under these fixed test conditions, the variation of CO conversion with time on line was measured using in-line infra-red detection. A decrease in CO conversion with time is indicative of loss of activity of the catalyst.

EXAMPLE 1

30 g of gamma alumina particles of size 0.6-1.0 mm and having a BET surface area of 350 m$^2$/g was dipped in 200 ml of an aqueous solution of lead(II) nitrate at 60 to 70° C. and of approximate concentration 6.8 g of lead(II) nitrate per 100 ml of solution. The material was removed from the solution after 20 minutes, drained, dried at 110° C. for two hours and then calcined in an oven at 300° C. for two hours. Analysis of the resultant material (Sample A) showed a lead content of 6.4% by weight.

EXAMPLE 2

Example 1 was repeated but using an aqueous solution containing 20.3 g of Pb(NO$_3$)$_2$ per 100 ml of solution. Chemical analysis of the resultant product (Sample B) showed a lead content of 10.7% by weight.

EXAMPLE 3

Example 1 was repeated but using an aqueous solution of approximate concentration 37 g of Pb(NO$_3$)$_2$ per 100 ml of solution. After calcination of the material at 300° C., the sample was re-dipped using a second aqueous solution containing about 37 g of Pb(NO$_3$)$_2$ per 100 ml of solution and then drained, dried at 110° C. for two hours and then calcined in an oven at 300° C. for two hours. Chemical analysis of this material (Sample C) gave a lead content of 19.9% by weight, and infra-red analysis showed that little of the lead nitrate had decomposed to lead oxide. A portion of Sample C was heated in air to 900° C. for over 2 hours to ensure complete decomposition of the lead compounds to lead oxide. The lead content after heating to 900° C. was 23.7% by weight.

EXAMPLE 4

A 1.5 M solution of Na$_2$CO$_3$ and 5 litres of a solution containing 1843 g of Al(NO$_3$)$_3$.9H$_2$O and 15.05 g of Pb(NO$_3$)$_2$ were heated to 80° C. and added to 1 litre of demineralised water at a temperature of 70° C. and at rates sufficient to maintain a pH of approximately 6.8. The resultant slurry was aged at 70° C. for 30 minutes, washed and filtered and then dried at 110° C. for 16 hours. The dried sample was then calcined in an oven at 300° C. for 6 hours, 2% graphite by weight was added and the resultant product formed into pellets of size 0.6-1.0 mm. The product had a lead content of 3.5% by weight. Despite the washing step the product (Sample D) had a residual sodium content of about 1.1% by weight. XRD analysis showed that the bulk of the lead was in a phase of structure similar to Mg$_4$Al$_2$(OH)$_{14}$.3H$_2$O and was therefore presumed to be a lead "aluminate". Also a phase of the structure 3PbO.2Pb(OH)$_2$ was present.

Samples of the guard bed materials were tested as described above. For purposes of a first comparison, (Comp X), the guard bed was 0.197 ml of the untreated gamma alumina particles as used for making the guard materials of Examples 1 to 3, and as a second comparison (Comp Y) the guard bed was 0.197 ml of the catalyst particles. For test method 1, the % CO conversion was determined for a period of over 5 days with measurements being taken at intervals of about 2-3 hours (about 6-7 hours for the guard bed material of Sample D). For test method 2, measurements were taken about every 6 hours over a period of 11 days. To assist comparison, the CO conversion measurements were plotted against time-on-line and a smooth curve drawn through the points for each Sample. (The individual points showed little variance from the smooth curves). From these plots, the conversion at regular intervals (every 6 hours for test method 1 and every 24 hours for test method 2) was determined and are shown in the following Tables 1 and 2 wherein the % CO conversion figures have been rounded to the nearest integer.

TABLE 1

Test method 1 - 5.2 ppm HCl

CO conversion (%)

| Time on line (hours) | Sample A | Sample B | Sample C | Sample D | Comp X | Comp Y |
|---|---|---|---|---|---|---|
| 6 | 92 | 92 | 92 | 92 | 92 | 95 |
| 12 | 90 | 91 | 91 | 90 | 92 | 94 |
| 18 | 90 | 90 | 90 | 89 | 90 | 92 |
| 24 | 89 | 90 | 89 | 89 | 85 | 90 |
| 30 | 84 | 88 | 88 | 88 | 76 | 87 |
| 36 | 78 | 85 | 87 | 88 | 66 | 83 |
| 42 | 70 | 80 | 86 | 87 | 50 | 78 |
| 48 | 61 | 72 | 86 | 85 | 27 | 70 |
| 54 | 47 | 62 | 85 | 81 | 4 | 57 |
| 60 | 29 | 47 | 84 | 76 | 1 | 40 |

It is seen from Table 1 that the guard bed materials of the invention have a similar effectiveness up to a time on line of about 30 hours, with the guard bed of Sample A being somewhat inferior, presumably as a result of its relatively low lead content. In this regard it is calculated that the amount of hydrogen chloride fed to the guard bed in 30 hours is approximately the amount required to convert all the lead in the guard bed of Sample B to lead(II) chloride. Sample D was superior to Sample B, despite having a much lower lead content. The alumina guard bed, Comp X, is initially as effective as the guard beds of the invention, presumably as a result of the reaction of hydrogen chloride with surface hydroxyl groups. However its performance rapidly deteriorates indicating that it has only a limited chloride capacity. The use of a sacrificial bed of catalyst as the guard bed, i.e. as in Comp Y, initially gives a superior performance to the guard beds of the invention as a result of the additional catalyst being available to catalyse the shift reaction (which is here operated under such a high space velocity that the reaction is activity rather than equilibrium limited—under the operating conditions, the carbon monoxide conversion required to reach equilibrium would be over 99%). However Comp Y shows that the performance of the catalyst rapidly falls off, albeit not so fast as using untreated alumina as the guard bed.

TABLE 2

Test method 2 - 1 ppm HCl

CO conversion (%)

| Time on line (hours) | Sample B | Sample C | Comp X | Comp Y |
|---|---|---|---|---|
| 24 | 87 | 87 | 85 | 91 |
| 48 | 85 | 85 | 78 | 86 |
| 72 | 83 | 83 | 62 | 77 |
| 96 | 82 | 82 | 26 | 55 |
| 120 | 75 | 80 | 3 | 17 |
| 144 | 60 | 79 | 0 | 0 |
| 168 | 29 | 78 | 0 | 0 |
| 192 | 4 | 76 | 0 | 0 |
| 216 | 0 | 75 | 0 | 0 |
| 240 | 0 | 72 | 0 | 0 |

Calculation shows that for Samples B and C in test method 2, significant de-activation commences when the total amount of HCl fed is equivalent to conversion of about 75% and 95% respectively of the to lead chloride. Again the lead-containing guard beds were more effective in guarding against de-activation than the use of a sacrificial bed of the catalyst.

EXAMPLE 5

80 g of chromia cylindrical pellets of diameter 5.6 mm and 4.9 mm length were dipped in 200 ml of an aqueous solution of lead(II) nitrate at room temperature and of approximate concentration 23.15 g of lead(II) nitrate per 100 ml of solution. The material was removed from the solution, drained and allowed to dry in flowing air at room temperature for 48 hours. Analysis of the resultant material (Sample E) showed a lead content of 6.6% by weight.

EXAMPLE 6

Example 5 was repeated and then the dried pellets were re-dipped, drained and dried as described in Example 5 a further two times. Analysis of the resultant material (Sample F) showed a lead content of 10.9% by weight.

EXAMPLE 7

For purposes of comparison (Comp Z) a sample of the chromia pellets as used in Example 5 were dipped in water and dried as described in Example 5.

The samples were tested as described above: before testing the pellets were ground to a particle size of 0.6-1.0 mm. The results are shown in the Table 3.

TABLE 3

Test method 1 - 5.2 ppm HCl

CO conversion (%)

| Time on line (hours) | Sample E | Sample F | Comp Z |
|---|---|---|---|
| 6 | 90 | 91 | 91 |
| 12 | 89 | 90 | 90 |
| 18 | 88 | 89 | 88 |
| 24 | 86 | 88 | 84 |
| 30 | 83 | 84 | 79 |
| 36 | 75 | 79 | 71 |
| 42 | 67 | 72 | 61 |
| 48 | 56 | 62 | 44 |

TABLE 3-continued

| | Test method 1 - 5.2 ppm HCl | | |
|---|---|---|---|
| Time on | CO conversion (%) | | |
| line (hours) | Sample E | Sample F | Comp Z |
| 54 | 42 | 48 | 21 |
| 60 | 22 | 30 | 3 |

It is seen from the Table 3 and by comparison with the data for Samples A and B in Table 1, that the chromia was a suitable support, but less effective than the gamma alumina of Samples A and B.

EXAMPLE 8

The Sample C was further tested as follows. In order to simulate a plant upset involving chloride contamination followed by steam condensation, the catalyst was reduced as described above and then the carbon monoxide shift conversion activity measured as described above. To simulate chloride contamination, for a period of 6 hours 5.2 ppm HCl was added to the gas mixture. The addition of HCl to the gas mixture was then stopped, and the reaction continued using the HCl-free gas for about a further 30 hours. Then the reaction temperature was decreased to 180° C. for 3 hours. Although this temperature is not low enough to cause condensation of the steam in the bulk phase, it is sufficiently low to cause some condensation of steam within the pores of the catalyst and guard bed. The temperature was then increased to 220° C. and maintained at that level for a further 15 hours.

The CO conversion decreased from an initial 95% to about 88% during the 6 hours that HCl was added to the gas mixture. Over the next 30 hours the conversion dropped slowly to about 85%. On decreasing the temperature to 180° C., the conversion fell rapidly to about 27%, but the conversion rapidly rose back to about 85% when the temperature was increased back to 220° C., indicating that no apparent lasting damage had been caused by the steam condensation.

For purposes of comparison, the above procedure was repeated using, in place of the lead-impregnated alumina granules, a commercial chloride-guard (Comp W) comprising alumina granules impregnated with sodium carbonate and calcined at above 500° C. to give granules of bulk density about 0.75 g/ml and a BET surface area of about 113 m$^2$/g which, after ignition at 900° C., had a sodium oxide, $Na_2O$ content of about 14% by weight. This was tested in the same manner. The carbon monoxide conversion fell from an initial value of 95% to 88% during the 6 hours that HCl was present in the gas mixture and then fell gradually to about 84% over the next 30 hours. On decreasing the temperature, the carbon monoxide conversion rapidly fell to under 20% but, unlike the lead-impregnated material, Sample C, did not recover upon increasing the temperature back to 220° C., but remained at below 20%.

EXAMPLE 9

259 g of gamma alumina particles of size 0.6-1.0 mm and having a BET surface area of 350 m$^2$/g was dipped in 800 ml of an aqueous solution of lead(II) nitrate at 60 to 70° C. and of approximate concentration 55 g of lead(II) nitrate per 100 ml of solution. The material was removed from the solution after 30 minutes, drained, dried at 110° C. for two hours. Part of the dried product was calcined in an oven at 150° C. for two hours to give Sample G, while the remainder was calcined in an oven at 200° C. for 2 hours to give Sample H.

XRD analysis of Sample G before and after it had been contacted at 220° C. with a steam/hydrogen/carbon dioxide/carbon monoxide/nitrogen gas mixture as used in the test procedure showed no change, indicating that under the test conditions, the lead nitrate is not reduced. Temperature programmed reduction analysis likewise indicated that no reduction occurred below 220° C.

EXAMPLE 10

303 g of gamma alumina particles of size 0.6-1.0 mm and having a BET surface area of 350 m$^2$/g was dipped in 800 ml of an aqueous solution of lead(II) nitrate at 60 to 70° C. and of approximate concentration 55 g of lead(II) nitrate per 100 ml of solution. The material was removed from the solution after 30 minutes, drained, dried at 110° C. for two hours and then calcined in an oven at 300° C. for two hours. The above process was repeated using the calcined lead nitrate impregnated alumina prepared as above and a fresh quantity of the lead nitrate solution. After calcination at 300° C., the resultant material was re-dipped for a third time, again using a fresh amount of the lead nitrate solution. The calcined material has a lead content of 25.5% by weight and was designated Sample J. After calcination at 300° C. for two hours, a portion of the Sample J was calcined at 400° C. for a further two hours to give Sample K and a second portion of Sample J was calcined at 550° C. for two hours to give Sample M.

Portions of Samples G, H, J, K and M were heated in air at 900° C. for over two hours to ensure decomposition of the lead nitrate to lead oxide. In each case a loss of weight was observed, indicating that prior to such heating at 900° C., a significant proportion of the lead-nitrate had not decomposed to lead oxide. The lead contents of the samples, before and after heating to 900° C. are set out in Table 4.

TABLE 4

| | | Pb content (% by weight) | |
|---|---|---|---|
| | Calcination temp. (° C.) | before heating at 900° C. | after heating at 900° C. |
| Sample G | 150 | 16.1 | 19.3 |
| Sample H | 200 | 16.3 | 19.4 |
| Sample J | 300 | 25.5 | 30.2 |
| Sample K | 300 + 400 | 27.7 | 30.1 |
| Sample M | 300 + 550 | 28.7 | 30.3 |

The Samples G, H, J, K and M, and also a commercially available catalyst (Sample N) comprising lead oxide supported on alumina and containing 20.4% by weight of lead, were tested as described above using 1 ppm HCl (test method 2). The results are shown in Table 5.

TABLE 5

| | Test method 2 - 1 ppm HCl | | | | | |
|---|---|---|---|---|---|---|
| Time on | CO conversion (%) | | | | | |
| line (hours) | G | H | J | K | M | N |
| 24 | 87 | 88 | 84 | 86 | 86 | 85 |
| 48 | 85 | 86 | 82 | 85 | 85 | 81 |
| 72 | 83 | 84 | 80 | 83 | 77 | 72 |

TABLE 5-continued

| | Test method 2 - 1 ppm HCl | | | | | |
|---|---|---|---|---|---|---|
| Time on | CO conversion (%) | | | | | |
| line (hours) | G | H | J | K | M | N |
| 96 | 81 | 83 | 78 | 82 | 57 | 50 |
| 120 | 80 | 82 | 76 | 80 | 13 | 7 |
| 144 | 79 | 80 | 74 | 79 | 0 | 0 |
| 168 | 76 | 75 | 73 | 78 | 0 | 0 |
| 192 | 60 | 55 | 72 | 76 | 0 | 0 |
| 216 | 27 | 12 | 68 | 75 | 0 | 0 |
| 240 | 3 | 1 | 58 | 73 | 0 | 0 |

By comparison with the data in Table 2, it is seen that, despite its high lead content, Sample N, lead oxide on alumina, is only marginally superior to Comp X, the alumina granules used to make the guard materials of the invention. Comparison of the performance of samples K and M, which were calcined at 400° C. and 550° C. respectively, shows that Sample M is significantly inferior to Sample K, and only slightly superior to Sample N, illustrating that calcination at 550° C. effected too much decomposition of the lead nitrate.

EXAMPLE 11

Example 10 was repeated but using lead acetate solutions containing 63 g of Pb(CH$_3$CO$_2$)$_2$.3H$_2$O per 100 ml in place of the lead nitrate solutions.

The samples after calcination at 300° C., 300° C.+400° C., and 300° C.+550° C., were designated Samples P, Q and R respectively and had lead contents of 34.3%, 34.6% and 34.9% by weight respectively. Infra-red analysis shows that in all of the Samples P, Q and R, the lead acetate had undergone partial decomposition, presumably to lead oxide. XRD analysis of Sample P after it had been contacted at 220° C. with a steam/hydrogen/carbon dioxide/carbon monoxide/nitrogen gas mixture as used in the test procedure showed that, under the test conditions, the lead species in Sample P is reduced to elemental lead.

The samples were tested as above (Test method 2) and the results are shown in Table 6.

TABLE 6

| | Test method 2 - 1 ppm HCl | | |
|---|---|---|---|
| Time on | CO conversion (%) | | |
| line (hours) | Sample P | Sample Q | Sample R |
| 24 | 87 | 82 | 86 |
| 48 | 82 | 77 | 82 |
| 72 | 69 | 64 | 74 |
| 96 | 43 | 41 | 58 |
| 120 | 0 | 3 | 26 |

It is seen by comparison with the data in Table 2 that lead acetate offers little advantage over the gamma alumina particles (Comp X).

I claim:

1. A process for performing a catalytic reaction involving hydrogen selected from the list consisting of hydrogenation reactions, methanol synthesis, methanol decomposition, the shift reaction and the reverse shift reaction, comprising passing a process gas containing carbon monoxide and steam through a guard bed of a particulate composition containing a) at least one lead compound, other than lead oxide, that reacts with hydrogen chloride and b) a support therefor, and then passing said process gas at a temperature in the range of 150-300° C. through a bed of copper-containing catalyst.

2. A process according to claim 1 wherein the process gas further comprises at least one gas selected from the group consisting of hydrogen, carbon dioxide, methane, and nitrogen.

3. A process according to claim 1 wherein the process gas is passed through the copper-containing bed at an inlet temperature in the range 150 to 250° C.

4. A process according to claim 1 wherein the process gas contains 1 to 4% by volume of carbon monoxide, and at least one mole of steam per mole of carbon monoxide.

5. A process according to claim 1 wherein the catalytic reaction is a shift reaction.

6. A process according to claim 1 wherein the copper catalyst is selected from the list consisting of a copper/zinc oxide/alumina or copper/zinc oxide/chromia catalyst.

7. A process according to claim 6 in which some of the zinc oxide is replaced by magnesia.

* * * * *